US00PP20371P2

(12) United States Plant Patent
Egger

(10) Patent No.: US PP20,371 P2
(45) Date of Patent: Sep. 29, 2009

(54) ***AGASTACHE* PLANT NAMED 'RASPBERRY SUMMER'**

(50) Latin Name: ***Agastache* sp.**
Varietal Denomination: Raspberry Summer

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/150,185

(22) Filed: Apr. 25, 2008

(51) Int. Cl.
*A01H 5/00* (2006.01)

(52) U.S. Cl. ..... Plt./399

(58) Field of Classification Search ..... Plt./399, Plt./263

See application file for complete search history.

*Primary Examiner*—Annette H. Para
*Assistant Examiner*—Susan B McCormick Ewoldt
(74) *Attorney, Agent, or Firm*—Klarquist Sparkman, LLP

(57) ABSTRACT

A new and distinct form of *Agastache* plant characterized by large, purple red flowers in large clusters, long bloom time, upright plant habit with dense branching, and excellent vigor.

1 Drawing Sheet

Botanical denomination: *Agastache* sp.
Variety designation: 'Raspberry Summer'.

BACKGROUND OF THE INVENTION

The present invention relates to a new and distinct cultivar of *Agastache*, given the name, 'Raspberry Summer'. *Agastache* is in the family Lamiaceae. The new cultivar is a F2 selection from a planned breeding program. The original cross was between a dwarf form of *Agastache pallidiflora* 'Pink Pop' (an unpatented plant) as the seed parent and a dark pink *Agastache cana* (an unpatented plant) as the pollen parent.

This plant exhibits the following characteristics:

1. Large, purple red flowers in large clusters,
2. Upright plant habit with dense branching,
3. Long bloom time,
4. Excellent vigor.

The new variety has been reproduced only by asexual propagation (cuttings and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a one-year-old *Agastache* 'Raspberry Summer' growing in the garden in mid summer in Canby, Oreg.

DETAILED PLANT DESCRIPTION

The following is a detailed description of the new *Agastache* cultivar based on observations of two-year-old specimen grown outside in the ground in the garden in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Form.*—Upright, herbaceous perennial.
*Cold hardiness.*—USDA Zone 6–9.
*Size.*—Grows to 70 cm tall and 60 cm wide.
*Vigor.*—Excellent.
*Stem.*—Square, grows to 8 mm wide and 30 cm tall before flowering, internodes 6 cm to 9 cm long, Yellow Green 147B, with lateral branching at each node.
*Roots.*—White 155B, fibrous, plants root easily from stem cuttings.

Leaf:

*Type.*—Simple.
*Arrangement.*—Opposite.
*Shape.*—Ovate.
*Venation.*—Pinnate.
*Margins.*—Crenate.
*Apex.*—Obtuse.
*Base.*—Cordate.
*Blade size.*—Grows to 5.5 cm long and 3 cm wide.
*Surface texture.*—Puberulous on both sides.
*Petiole description.*—Grows to 3 cm long and 1.2 mm wide, puberulous, Green 137D.
*Leaf color.*—Topside Green 137A, bottom side Greyed Green 191A.

Inflorescence:

*Type.*—Terminal spike.
*Number of flowers.*—About 140 per spike in 7 to 12 usually congested whorls.
*Peduncle.*—24 cm to 50 cm tall and 3 mm wide, puberulous, Green 137B.
*Pedicel.*—1 mm to 2 mm long, puberulous, Yellow Green 147B.
*Bloom period.*—June through frost in Canby, Oreg.

Flower bud:

*Size.*—17 mm long and 3.5 mm wide at the widest point prior to opening.

*Description.*—Tubular.

*Surface texture.*—Pubescent.

*Color.*—Red Purple 60A.

Flower:

*Type.*—Zygomorphic.

*Shape.*—Bilabiate, tubular.

*Size.*—3 cm long and 9 mm wide.

*Corolla description.*—3 cm long and spreads to 9 mm wide, color changes from Red Purple 60C when just open to Red Purple 71A inside and out, pubescent inside and out, tube 2.3 cm long and 1 mm to 4 mm wide; 2 upper lobes joined at top, together 5 mm long and 5 mm wide, acute, entire; three lower lobes, two spreading sideways, the terminal lobe broad, reflexed, cupped, obcordate and mucronate, entire, 7 mm wide and 6 mm deep, two side lobes 4 mm long and 3 mm wide.

*Calyx description.*—9 mm long and 2.5 mm wide, color closest to Greyed Green 191 A, pubescent outside and glabrous inside, 5 lobed, lobes narrow, 2 mm long, entire, acuminate.

*Pistil description.*—1 in number, 36 mm long, ovary 0.5 mm long, Yellow Green 146C, style and stigma 35.5 mm long, Red Purple 61A at the tip to White 155D at base.

*Stamen description.*—4 in number, paired, exerted and reflexed, filaments 13 mm long, Purple 70A, anthers 1 mm long, Greyed Red 182D, pollen White 155D.

*Fragrance.*—Strong, herbal.

*Lastingness.*—A spike blooms for about 3 weeks on the plant.

Fruit: 4 nutlets, Green 144A.

Seed: Oblong, 1.5 mm long, Black 202A, fertile.

Pests and diseases: *Agastache* are known to be susceptible to mildew and rust in dry summer months. The new cultivar has no known resistances but has shown no problems in Canby, Oreg.

Comparisons: Compared to *Agastache* 'Pink Pop' dwarf, an unpatented plant and the seed parent, the new variety has purplish red rather than pink flowers with darker calyces, larger flowers and inflorescences.

Compared to a dark pink *Agastache cana*, an unpatented plant and the pollen parent, the new variety has denser inflorescences, with purplish red rather than dark pink flower color, and a more compact habit.

Compared to *Agastache* 'Summer Love', a sibling (co-pending U.S. Plant patent application Ser. No. 12/150,186), the new variety is shorter and has red purple flowers rather than vivid purple flowers.

Compared to *Agastache* 'Acapulco Salmon & Pink' (U.S. Plant Pat. No. 16,023), the new variety has purple red flowers rather than salmon pink to light purple. In addition, the new variety has a tighter and more upright habit.

I claim:

1. A new and distinct form of *Agastache* plant, substantially as shown and described.

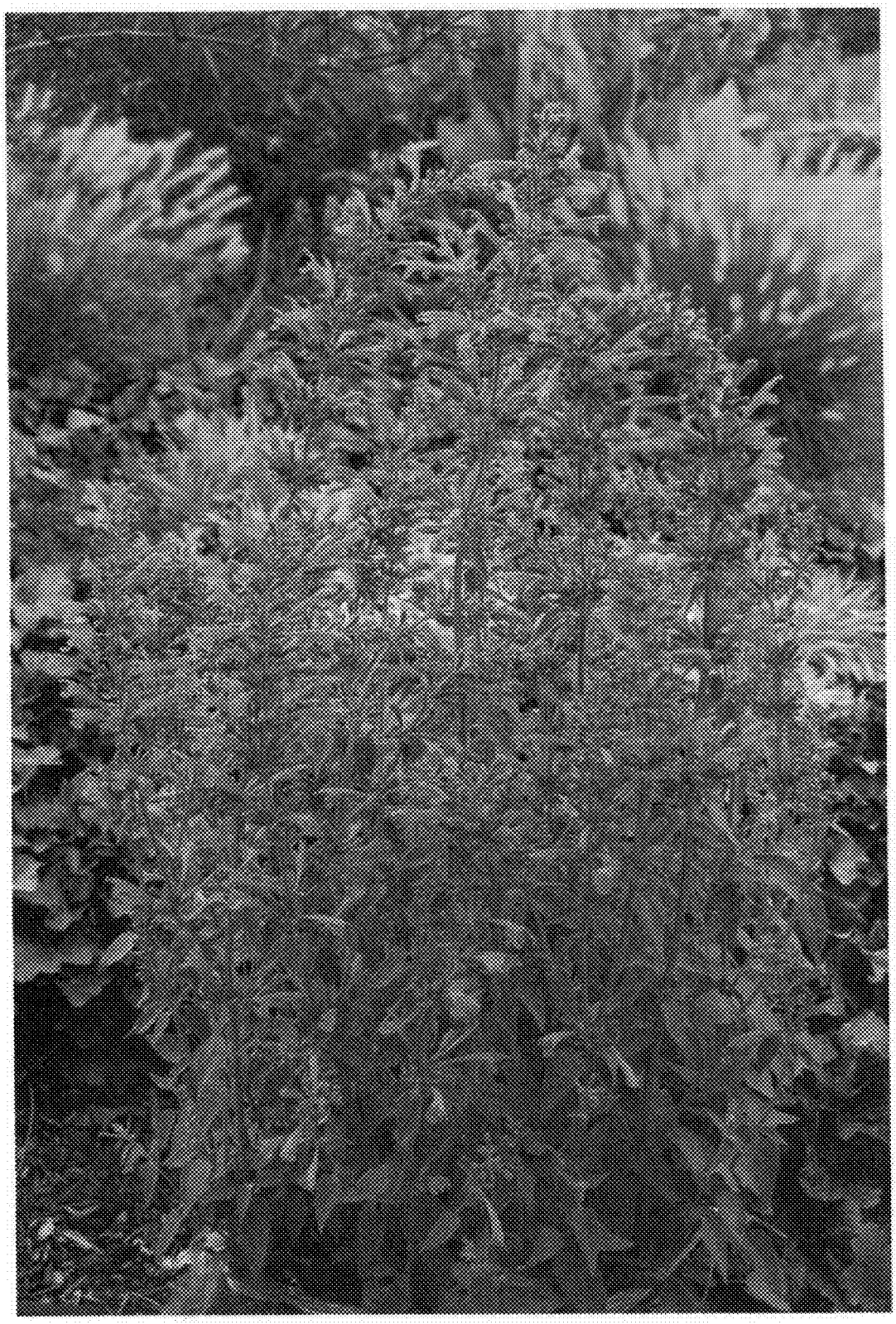

* * * * *